United States Patent
Van de Stolpe et al.

(10) Patent No.: US 11,674,185 B2
(45) Date of Patent: Jun. 13, 2023

(54) METHODS OF PROGNOSIS IN HIGH-GRADE SEROUS OVARIAN CANCER

(71) Applicant: KONINKLIJKE PHILIPS N.V., Eindhoven (NL)

(72) Inventors: Anja Van de Stolpe, Vught (NL); Wilhelmus Franciscus Johannes Verhaegh, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 43 days.

(21) Appl. No.: 16/864,518

(22) Filed: May 1, 2020

(65) Prior Publication Data

US 2020/0347460 A1    Nov. 5, 2020

Related U.S. Application Data

(60) Provisional application No. 62/842,557, filed on May 3, 2019.

(30) Foreign Application Priority Data

Oct. 22, 2019  (EP) .................... 19204471

(51) Int. Cl.
  *C12Q 1/6886*  (2018.01)
  *C12Q 1/6809*  (2018.01)
(52) U.S. Cl.
  CPC ......... *C12Q 1/6886* (2013.01); *C12Q 1/6809* (2013.01); *C12Q 2600/118* (2013.01); *C12Q 2600/158* (2013.01); *C12Q 2600/16* (2013.01)
(58) Field of Classification Search
  None
  See application file for complete search history.

(56) References Cited

U.S. PATENT DOCUMENTS

| 2010/0216137 A1 | 8/2010 | Bankaitis-Davis et al. |
| 2016/0117443 A1* | 4/2016 | Van Ooijen ............ G16B 25/10 514/249 |
| 2017/0009303 A1 | 1/2017 | Ahuja et al. |
| 2017/0046477 A1 | 2/2017 | Van Ooijen |

OTHER PUBLICATIONS

Cobb et al (Crit Care Med 2002 vol. 30 p. 2711) (Year: 2002).*
Dijkers, P.F. et al., (2000). Expression of the pro-apoptotic bcl-2 family member bim is regulated by the forkhead transcription factor FKHR-L1. Curr Biol 10: 1201-1204 (2000).
Miammucari, C. et al., "Fox03 controls autophagy in skeletal muscle in vivo". Cell Metab 6: 458-471, Dec. 2007.
Kaltschmidt, B. et al., "The pro-or anti-apoptotic function of NF-kappaB is determined by the nature of the apoptotic stimulus". Eur J Biochem. Jun. 2000; 267(12):3828-35.
Van Ooijen, H. et al., "Assessment of functional phosphatidylinositol 3-kinase pathway activity in cancer tissue using forkhead box-O target gene expression in a knowledge-based computational model". The American Journal of Pathology, vol. 188, No. 9, Sep. 2018.
Van de Stolpe, A. "Quantitative measurement of functional activity of the PI3K signaling pathway in cancer". Cancers 2019, 11, 293; doi:10.3390/cancers 11030293.

* cited by examiner

*Primary Examiner* — Katherine D Salmon

(57) ABSTRACT

The present application mainly relates to a method for determining a prognosis for a subject diagnosed with high-grade serous ovarian cancer. The method comprises determining the prognosis based on activities of at least two cellular signaling pathways including a phosphatidylinositide 3-kinase (PI3K) pathway and a nuclear factor-kappa B (NFkB or NFκB) pathway in a sample of the subject. The present application also relates to a method for identifying a subject diagnosed with high-grade serous ovarian cancer that will be suitable for a PI3K pathway targeting therapy or an NFkB pathway targeting therapy. The method comprises identifying the subject based on activities of at least two cellular signaling pathways including a PI3K pathway and an NFkB pathway in a sample of the subject. The present application further relates to corresponding apparatuses, non-transitory storage media, computer programs and kits.

8 Claims, 5 Drawing Sheets

METHODS OF PROGNOSIS IN HIGH-GRADE SEROUS OVARIAN CANCER

CROSS-REFERENCE TO RELATED APPLICATIONS

This patent application claims the priority benefit under 35 U.S.C. § 119(e) of U.S. Provisional Application No. 62/842,557, filed on May 3, 2019, and European Patent Application No. 19204471.7 filed on Oct. 22, 2019, the contents of which are herein incorporated by reference.

FIELD OF THE INVENTION

The subject matter described herein mainly relates to bioinformatics, genomic processing arts, proteomic processing arts, and related arts. More particularly, the present invention relates to a method for determining a prognosis for a subject diagnosed with high-grade serous ovarian cancer, and to a method for identifying a subject diagnosed with high-grade serous ovarian cancer that will be suitable for a PI3K pathway targeting therapy or an NFkB pathway targeting therapy. The present invention further relates to an apparatus, a non-transitory storage medium and a computer program for determining a prognosis for a subject diagnosed with high-grade serous ovarian cancer, or for identifying a subject diagnosed with high-grade serous ovarian cancer that will be suitable for a PI3K pathway targeting therapy or an NFkB pathway targeting therapy. The present invention further relates to a kit for determining a prognosis for a subject diagnosed with high-grade serous ovarian cancer, or for identifying a subject diagnosed with high-grade serous ovarian cancer that will be suitable for a PI3K pathway targeting therapy or an NFkB pathway targeting therapy. Finally, the present invention relates to a use of the kit in performing any of the above-mentioned methods. The prognosis and the identification are performed based on a combination of cellular signaling pathway activities.

BACKGROUND OF THE INVENTION

Ovarian cancer (OVC) is the most lethal gynecological malignancy and one or the most common causes of cancer mortality of women worldwide. The most common and deadliest subtype of ovarian cancer is high-grade serous ovarian cancer (HGSOC), which accounts for approximately 75% of ovarian cancer. For treatment of high-grade serous ovarian cancer, standard chemotherapy is used in addition to surgical debulking, in which the bulk of the tumor load is taken away. Chemotherapy regimens generally contain cisplatin or carboplatin, but a number of patients have found to show resistance to these compounds. Following standard chemotherapy treatment after debulking surgery, the disease-free survival (DFS) of high-grade serous ovarian cancer varies greatly, and currently there is no method to distinguish between patients with a bad prognosis and a short disease-free survival and patients with a better prognosis and a longer disease-free survival.

SUMMARY OF THE INVENTION

In accordance with an aspect, the present invention relates to a method for determining a prognosis for a subject diagnosed with high-grade serous ovarian cancer, wherein the method comprises:

determining the prognosis based on activities of at least two cellular signaling pathways including a phosphatidylinositide 3-kinase (PI3K) pathway and a nuclear factor-kappa B (NFkB or NFκB) pathway in a sample of the subject, wherein said cellular signaling pathway activities are based on the expression levels of three or more target genes for said cellular signaling pathways, and wherein:

the three or more PI3K target genes are selected from the group consisting of: AGRP, BCL2L11, BCL6, BNIP3, BTG1, CAT, CAV1, CCND1, CCND2, CCNG2, CDK 1A, CDK 1B, ESR1, FASLG, FBX032, GADD45A, INSR, MXI1, NOS3, PCK1, POMC, PPARGCIA, PRDX3, RBL2, SOD2 and TNFSF10, or from the group consisting of: ATP8A1, BCL2L11, BNIP3, BTG1, C10orf10, CAT, CBLB, CCND1, CCND2, CDKNIB, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10, or from the group consisting of: SOD2, BNIP3, MXI1, PCK1, PPARGC1A and CAT, and the three or more NFkB target genes are selected from the group consisting of: BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1, and wherein, when the activity of the PI3K pathway is low and the activity of the NFkB pathway is high, the prognosis is favorable, and wherein, when the activity of the PI3K pathway is high and the activity of the NFkB pathway is low, the prognosis is unfavorable, and wherein, when the activity of the PI3K pathway is low and the activity of the NFkB pathway is low or when the activity of the PI3K pathway is high and the activity of the NFkB pathway is high, the prognosis is intermediate.

The present invention is based on the inventors' insight that the analysis of cellular signaling pathway activities including the activities of a PI3K pathway and an NFkB pathway can be used to characterize high-grade serous ovarian cancer. In particular, the pathway activities were found to be suited for determining a prognosis for a subject diagnosed with high-grade serous ovarian cancer and/or for identifying a subject diagnosed with high-grade serous ovarian cancer that will be suitable for a PI3K pathway targeting therapy or an NFkB pathway targeting therapy (see below).

The term "prognosis", as used herein, refers to the likelihood or expectation of a clinical outcome, such as disease recurrence, disease progression, disease occurrence, and death caused by the disease, including but not limited to whether the signs and symptoms will improve or worsen (and how quickly) or remain stable over time or whether the subject survives.

In some embodiments, the prognosis is defined in a quantitative manner in several ways, as for example: "time to recurrence (of a disease), "time to progression (of a disease)", "time of occurrence (of a disease)", or "time to death (disease)".

In other embodiments, the prognosis is defined in a qualitative manner, as for example: "favorable", "intermediate" or "unfavorable". The clinical outcome can be favorable, intermediate or unfavorable, either in an absolute setting, i.e., for example, more or less than or approximately equal to a certain period of time (e.g., months or years) survival, or relative to another clinical condition, in comparison to which the clinical outcome can be favorable, intermediate, or unfavorable.

In some embodiments, the prognosis is the likelihood or expectation of disease-free survival. The likelihood or expectation of disease-free survival can be defined in a quantitative manner, as for example: the time period (e.g., in months or years) between last treatment and disease recurrence, or in a qualitative manner, as for example: "favorable", "intermediate" or "unfavorable" in an absolute or relative setting as stated above.

In some embodiments, the prognosis is the likelihood or expectation of overall disease-specific survival. The likelihood or expectation of overall disease-specific survival can be defined in a quantitative manner, as for example: the time period (e.g., months or years) of survival, or in a qualitative manner, as for example: "favorable", "intermediate" or "unfavorable" in an absolute or relative setting as stated above.

The term "subject", as used herein, refers to any living being. In some embodiments, the subject is an animal, preferably a mammal. In some embodiments, the subject is a human being, preferably a medical subject. In some embodiments, the subject is a human being that has been diagnosed as having high-grade serous ovarian cancer.

The "sample" may be an extracted sample, that is, a sample that has been extracted from the subject. Examples of the sample include, but are not limited to, a tissue, cells, blood and/or a body fluid such as a bronchial aspirate, bone marrow aspirate or a sample drawn from a body cavity of a subject.

The term "activity of a (specific) pathway", as used herein, refers to the activity of a cellular signaling pathway associated transcription factor (TF) element in the sample, the TF element controlling transcription of target genes, in driving the target genes to expression, i.e., the rate by which the target genes are transcribed, e.g., in terms of a high activity (i.e., a high rate, or a rate higher than a certain rate) or a low activity (i.e., a low rate, or a rate lower than a certain rate), or respective scores, values or parameters related to such activity. The transcription factor activity is a readout for activity of the associated pathway. The pathway activity may be represented by, for example, an activity level. The activity of each of the pathways may be determined in a quantitative manner as a numerical value or in a qualitative manner as for example "high" or "low". A high (or low) activity of a pathway may refer to the activity being higher (or lower) than a defined threshold or higher (or lower) than the activity determined in a sample of a healthy subject or a subject having a certain clinical condition.

The transcription factor (TF) element of the NFkB pathway preferably consists of a protein complex containing at least one or, preferably, a dimer of the NFkB members (NFKB1 or p50/p105, NFKB2 or p52/p100, RELA or p65, REL, and RELB), which is capable of binding to specific DNA sequences, thereby controlling transcription of target genes.

The transcription factor (TF) element of the PI3K pathway preferably consists of at least a FOXO family member. As the PI3K pathway negatively regulates the tumor suppressive FOXO transcription factor, the activity of the FOXO TF element is substantially negatively or inversely correlated with the activity of the PI3K pathway (on the premise that there is no oxidative stress (see, for example, van Ooijen H. et al., "Assessment of Functional Phosphatidylinositol 3-Kinase Pathway Activity in Cancer Tissue Using Forkhead Box-O Target Gene Expression in a Knowledge-Based Computational Model", American Journal of Pathology, Vol. 188, No. 9, September 2018, pages 1956 to 1972)).

The determination of the prognosis may be performed by means of a mathematical model, in particular, a calibrated mathematical model, or by means of a decision model as exemplified in Table 1. The determination of the prognosis may comprise (i) receiving activities of the pathways and (ii) determining the prognosis, the determining being based on evaluating a (calibrated) mathematical model relating the activities of the pathways to a score indicative for the prognosis, or the decision model as exemplified in Table 1.

The method of the first aspect of the present application may be a computer-implemented method.

It is preferred that, when the activity of the PI3K pathway is low and the activity of the NFkB pathway is high, the prognosis is favorable.

It is further preferred that, when the activity of the PI3K pathway is high and the activity of the NFkB pathway is low, the prognosis is unfavorable.

Yet further, it is preferred that, when the activity of the PI3K pathway is low and the activity of the NFkB pathway is low or when the activity of the PI3K pathway is high and the activity of the NFkB pathway is high, the prognosis is intermediate.

In some embodiments, the determination of the prognosis is based on the activity of the PI3K pathway and the activity of the NFkB pathway. In other embodiments, the determination of the prognosis is based on the activity of the PI3K pathway, the activity of the NFkB pathway and the activity of a further cellular signaling pathway or the activities of yet further cellular signaling pathways.

The activity of a pathway, e.g., in a cell or tissue sample isolated from the subject, can be determined by pathway analysis.

Pathway analysis enables a quantitative measurement of pathway activity in a sample of a subject based on inferring the activity of a cellular signal pathway from measurements of mRNA levels of target genes of the transcription factor associated with the respective cellular signaling pathway (see, for example, Verhaegh W. et al., "Selection of personalized patient therapy through the use of knowledge-based computational models that identify tumor-driving signal transduction pathways", Cancer research, Vol. 74, No. 11, June 2014, pages 2936 to 2945, as well as Verhaegh W. and van de Stolpe A., "Knowledge-based computational models", Oncotarget, Vol. 5, No. 14, July 2014, pages 5196 and 5197).

The determining of the activity of the PI3K pathway or of the NFkB pathway can be performed as described for example in the following documents, each of which is hereby incorporated in its entirety for reference: Published international patent applications WO 2013/011479 (titled "Assessment of cellular signaling pathway activity using probabilistic modeling of target gene expression"), WO 2014/102668 (titled "Assessment of cellular signaling pathway activity using linear combination(s) of target gene expressions"), WO 2015/101635 (titled "Assessment of PI3K cellular signaling pathway activity using mathematical modelling of target gene expression"), WO 2016/062892 (titled "Medical prognosis and prediction of treatment response using multiple cellular signaling pathway activities"), WO 2016/062893 (titled "Medical prognosis and prediction of treatment response using multiple cellular signaling pathway activities"), WO 2017/029215 (titled "Assessment of NFkB cellular signaling pathway activity using mathematical modelling of target gene expression"), and WO 2018/096076 (titled "Method to distinguish tumor suppressive FOXO activity from oxidative stress").

Suitable target genes for the determination of pathway activity are indicated in the above-mentioned references. In this respect, particular reference is also made to the sequence listings for the target genes provided with the above-mentioned references.

Thus, the three or more PI3K target genes, e.g. three, four, five, six, seven eight, nine, ten, eleven, twelve, thirteen, fourteen, fifteen, sixteen, seventeen, eighteen, nineteen or more, are preferably selected from the group consisting of: AGRP, BCL2L11, BCL6, BNIP3, BTG1, CAT, CAV1, CCND1, CCND2, CCNG2, CDK1A, CDK1B, ESR1, FASLG, FBX032, GADD45A, INSR, MXI1, NOS3, PCK1, POMC, PPARGCIA, PRDX3, RBL2, SOD2 and TNFSF10 (WO 2015/101635), or from the group consisting of: ATP8A1, BCL2L11, BNIP3, BTG1, C10orf10, CAT, CBLB, CCND1, CCND2, CDKNIB, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10 (WO 2016/062892, WO 2016/062893), or from the group consisting of: SOD2, BNIP3, MXI1, PCK1, PPARGC1A and CAT (WO 2018/096076), and/or the three or more NFkB target genes, e.g. three, four, five, six, seven eight, nine, ten, eleven, twelve, thirteen, fourteen, fifteen, sixteen, seventeen, eighteen, nineteen or more, are preferably selected from the group consisting of: BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1 (WO 2017/029215).

For use in the pathway analysis, three or more, for example, three, four, five, six, seven, eight, nine, ten, eleven, twelve, thirteen, fourteen, fifteen, sixteen, seventeen, eighteen, nineteen or more, target genes of each assessed cellular signaling pathway can be analyzed to determine pathway activities.

Preferably, the activities of the at least two cellular signaling pathways in the sample are inferred or are inferable by a method comprising:

receiving expression levels of three or more, for example, three, four, five, six, seven, eight, nine, ten, eleven, twelve, thirteen, fourteen, fifteen, sixteen, seventeen, eighteen, nineteen or more, target genes of each of the respective cellular signaling pathways measured in the sample, determining an activity level of a cellular signaling pathway associated transcription factor (TF) element, the cellular signaling pathway associated TF element controlling transcription of the three or more target genes, the determining being based on evaluating a calibrated mathematical pathway model relating the expression levels of the three or more target genes to the activity level of the TF element, and, inferring the activity of the respective cellular signaling pathway based on the determined activity level of the cellular signaling pathway associated TF element.

The three or more target target genes are preferably selected from the groups listed above.

It is preferred that the calibrated mathematical pathway model is a probabilistic model, preferably a Bayesian network model, based on conditional probabilities relating the activity level of the TF element and the expression levels of the three or more target genes, or that the mathematical pathway model is based on one or more linear combination(s) of the expression levels of the three or more target genes.

This is described in detail in the published international patent applications WO 2013/011479 ("Assessment of cellular signaling pathway activity using probabilistic modeling of target gene expression") and WO 2014/102668 ("Assessment of cellular signaling pathway activity using linear combination(s) of target gene expressions"), the contents of which are herewith incorporated in their entirety. Further details regarding the inferring of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

The definitions of and the embodiments related to "prognosis", "subject", "sample", "pathway activity", and "inferring a (PI3K or NFkB) pathway activity", as described above, are applicable to other aspects of the present application.

In accordance with a second aspect, the present invention relates to a method for identifying a subject diagnosed with high-grade serous ovarian cancer that will be suitable for a PI3K pathway targeting therapy or an NFkB pathway targeting therapy, wherein the method comprises:

identifying the subject based on activities of at least two cellular signaling pathways including a phosphatidylinositide 3-kinase (PI3K) pathway and a nuclear factor-kappa B (NFkB or NFκB) pathway in a sample of the subject, wherein said cellular signaling pathway activities are based on the expression levels of three or more target genes for said cellular signaling pathways, and wherein:

the three or more PI3K target genes are selected from the group consisting of: AGRP, BCL2L11, BCL6, BNIP3, BTG1, CAT, CAV1, CCND1, CCND2, CCNG2, CDK 1A, CDK 1B, ESR1, FASLG, FBX032, GADD45A, INSR, MXI1, NOS3, PCK1, POMC, PPARGCIA, PRDX3, RBL2, SOD2 and TNFSF10, or from the group consisting of: ATP8A1, BCL2L11, BNIP3, BTG1, C10orf10, CAT, CBLB, CCND1, CCND2, CDKNIB, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10, or from the group consisting of: SOD2, BNIP3, MXI1, PCK1, PPARGC1A and CAT, and the three or more NFkB target genes are selected from the group consisting of: BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1.

The term "PI3K pathway targeting therapy", as used herein, refers to a therapy that by means of a drug targets the PI3K or FOXO pathway or a member of the FOXO family and mediates the activity of the PI3K or FOXO pathway.

The term "NFkB pathway targeting therapy", as used herein, refers to a therapy that by means of a drug targets the NFkB pathway and mediates or in particular inhibits the activity of the NFkB pathway.

The subject of this aspect of the present invention has been diagnosed as having high-grade serous ovarian cancer, but would have a favorable prognosis if a PI3K pathway targeting therapy or an NFkB pathway targeting therapy is provided to the subject, or, in particular, if a PI3K pathway targeting drug or an NFkB pathway targeting drug is administered to the subject, or if besides said therapy, additional therapy is provided to the subject.

The PI3K pathway targeting therapy induces cell cycling, and by this means sensitizes the tumor cells to other treatments, e.g., chemotherapy, e.g. cisplatin, or radiation, which require dividing cells to be effective as cancer treatment. NFkB pathway-targeting therapy may have a similar effect to block apoptosis, for example, to increase sensitivity to radiation or chemotherapy. A PI3K pathway targeting therapy is preferable, since it is more effective.

The determination of the prognosis may be performed by means of a mathematical model, in particular, a calibrated mathematical model, or by means of a decision model. The identification of the subject may comprise (i) receiving activities of the pathways and (ii) identifying the subject, the identifying being based on evaluating a (calibrated) mathematical model relating the activities of the pathways to a score indicative for the subject that will be suitable for a PI3K pathway targeting therapy or an NFkB pathway targeting therapy, or the decision model.

The method of the second aspect of the present application may be a computer-implemented method.

It is preferred that, when the activity of the PI3K pathway is low and the activity of the NFkB pathway is high, the subject is identified as being suitable for a PI3K pathway targeting therapy or an NFkB pathway targeting therapy.

In some embodiments, the identification of the subject that will be suitable for a PI3K pathway targeting therapy or an NFkB pathway targeting therapy is based on the activity of the PI3K pathway and the activity of the NFkB pathway. In other embodiments, the identification of the subject that will be suitable for a PI3K pathway targeting therapy or an NFkB pathway targeting therapy is based on the activity of the PI3K pathway, the activity of the NFkB pathway and the activity of a further cellular signaling pathway or the activities of yet further cellular signaling pathways.

Preferably, the method further comprises:

providing to the identified subject the PI3K pathway targeting therapy or the NFkB pathway targeting therapy.

Preferably, the activities of the at least two cellular signaling pathways in the sample are inferred or are inferable by a method comprising:

receiving expression levels of three or more, for example, three, four, five, six, seven, eight, nine, ten, eleven, twelve, thirteen, fourteen, fifteen, sixteen, seventeen, eighteen, nineteen or more, target genes of each of the respective cellular signaling pathways measured in the sample, determining an activity level of a cellular signaling pathway associated transcription factor (TF) element, the cellular signaling pathway associated TF element controlling transcription of the three or more target genes, the determining being based on evaluating a calibrated mathematical pathway model relating the expression levels of the three or more target genes to the activity level of the TF element, and, inferring the activity of the respective cellular signaling pathway based on the determined activity level of the cellular signaling pathway associated TF element.

The three or more target target genes are preferably selected from the groups listed above.

It is preferred that the calibrated mathematical pathway model is a probabilistic model, preferably a Bayesian network model, based on conditional probabilities relating the activity level of the TF element and the expression levels of the three or more target genes, or that the mathematical pathway model is based on one or more linear combination(s) of the expression levels of the three or more target genes.

In accordance with a third aspect, the present invention relates to an apparatus for determining a prognosis for a subject diagnosed with high-grade serous ovarian cancer comprising a digital processor configured to perform the method of the first aspect of the invention, or for identifying a subject diagnosed with high-grade serous ovarian cancer that will be suitable for a PI3K pathway targeting therapy or an NFkB pathway targeting therapy comprising a digital processor configured to perform the method of the second aspect of the invention.

In accordance with a fourth aspect, the present invention relates to a non-transitory storage medium for determining a prognosis for a subject diagnosed with high-grade serous ovarian cancer storing instructions that are executable by a digital processing device to perform the method of the first aspect of the invention, or for identifying a subject diagnosed with high-grade serous ovarian cancer that will be suitable for a PI3K pathway targeting therapy or an NFkB pathway targeting therapy storing instructions that are executable by a digital processing device to perform the method of second aspect of the invention. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with a fifth aspect, the present invention relates to a computer program for determining a prognosis for a subject diagnosed with high-grade serous ovarian cancer comprising program code means for causing a digital processing device to perform a method of the first aspect of the invention, when the computer program is run on the digital processing device, or for identifying a subject diagnosed with high-grade serous ovarian cancer that will be suitable for a PI3K pathway targeting therapy or an NFkB pathway targeting therapy comprising program code means for causing a digital processing device to perform a method of the second aspect of the invention, when the computer program is run on the digital processing device. The digital processing device may be a handheld device (e.g., a personal data assistant or smartphone), a notebook computer, a desktop computer, a tablet computer or device, a remote network server, or so forth.

In accordance with a sixth aspect, the present invention relates to a kit for determining a prognosis for a subject diagnosed with high-grade serous ovarian cancer, or for identifying a subject diagnosed with high-grade serous ovarian cancer that will be suitable for a PI3K pathway targeting therapy or an NFkB pathway targeting therapy, the kit comprising:

components for measuring expression levels of six or more, for example, six, seven, eight, nine, ten, eleven, twelve, thirteen, fourteen, fifteen, sixteen, seventeen, eighteen, nineteen or more, target genes of each of at least two cellular signaling pathways including the PI3K pathway and the NFkB pathway in a sample of the subject, wherein the components comprises primers and probes for determining the expression levels of the six or more target genes for each cellular signaling pathway, and wherein the six or more PI3K target genes (for example, six, seven, eight, nine, ten, eleven, twelve, thirteen, fourteen, fifteen, sixteen, seventeen, eighteen, nineteen or more) are selected from the group consisting of: AGRP, BCL2L11, BCL6, BNIP3, BTG1, CAT, CAV1, CCND1, CCND2, CCNG2, CDK 1A, CDK 1B, ESR1, FASLG, FBX032, GADD45A, INSR, MXI1, NOS3, PCK1, POMC, PPARGCIA, PRDX3, RBL2, SOD2 and TNFSF10, or from the group consisting of: ATP8A1, BCL2L11, BNIP3, BTG1, C10orf10, CAT, CBLB, CCND1, CCND2, CDKNIB, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10, or from the group consisting of: SOD2, BNIP3, MXI1, PCK1, PPARGC1A and CAT, and the six or more NFkB target genes (for example, six, seven, eight, nine, ten, eleven, twelve, thirteen, fourteen, fifteen, sixteen, seventeen, eighteen, nineteen or more) are selected from the group consisting of: BCL2L1, BIRC3, CCL2, CCL3, CCL4, CCL5, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STAT5A, TNF, TNFAIP2, TNIP1, TRAF1, and VCAM1, and optionally the apparatus of the third aspect of the invention, the non-transitory storage medium of the fourth aspect of the invention, or the computer program of the fifth aspect of the invention.

The three or more target target genes are preferably selected from the groups listed above.

In accordance with a seventh aspect, the present invention relates to a use of the kit sixth aspect of the invention in performing the method of any of the first or the second aspect of the invention.

The components for measuring the expression levels of the three or more target genes of the respective cellular signaling pathway can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers.

In some embodiments, the kit includes a set of (labeled) probes directed to a portion of an mRNA or cDNA sequence of the three or more target genes as described above.

In some embodiments, the kit includes a set of primers and probes directed to a portion of an mRNA or cDNA sequence of the three or more target genes as described above.

Further advantages will be apparent to those of ordinary skill in the art upon reading and understanding the attached figures, the following description and, in particular, upon reading the detailed examples provided herein below.

In the method for identifying a subject diagnosed with high-grade serous ovarian cancer that will be suitable for a PI3K pathway targeting therapy or an NFkB pathway targeting therapy, the activities of the at least two cellular signaling pathways in the sample may be inferred or may be inferable by the same method as described for the method for determining a prognosis for a subject diagnosed with high-grade serous ovarian cancer and the same target genes as described above may be used.

One advantage of the present invention resides in a clinical decision support system that is configured to determine a prognosis for a subject diagnosed with high-grade serous ovarian cancer, e.g., a likelihood or expectation of disease recurrence, disease progression, disease occurrence, and death caused by the disease, based on a combination of pathway activities as described herein.

Another advantage of the present invention resides in a clinical decision support system that is configured to identify a subject diagnosed with high-grade serous ovarian cancer that will be suitable for a PI3K pathway targeting therapy or an NFkB pathway targeting therapy based on a combination of pathway activities as described herein.

Further advantages will be apparent to those of ordinary skill in the art upon reading and understanding the attached figures, the following description and, in particular, upon reading the detailed examples provided herein below.

It shall be understood that the methods of the first and the second aspect, the apparatus of the third aspect, the non-transitory storage medium of the fourth aspect, the computer program of the fifth aspect, the kit of the sixth aspect and the use of the kits of the seventh aspect have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIG. 3: Cluster groups 1 and 2. FIG. 4: Results for groups 1 to 3 together, according to cluster designation. (In both diagrams, the black circles represent C1 patients and the white circles represent C2 patients.)

DETAILED DESCRIPTION OF EMBODIMENTS

The following embodiments merely illustrate particularly preferred methods and selected aspects in connection there-with. The teaching provided therein may be used for constructing several tests and/or kits. The following examples are not to be construed as limiting the scope of the present invention.

Examples

The publicly available dataset GSE9891 (238 high-grade serous (HGS), 14 high-grade endometrioid (HGE), 11 low-grade serous or endometrioid (LG) and 18 low-malignant potential (LMP) ovarian cancers; see Tothill R. W. et al., "Novel molecular subtypes of serous and endometrioid ovarian cancer linked to clinical outcome", Clinical Cancer Research, Vol. 14, No. 16, August 2008, pages 5198 to 5208) was used.

From this dataset, only sample data from patients with high-grade serous ovarian cancer were selected. All samples had been obtained prior to treatment and had clinical annotations with regard to disease-free survival available.

Using pathway analysis on these Affymetrix HG-U133 Plus2.0 data, pathway activity scores for the NFkB pathway as well as for the FOXO transcription factor were measured and interpreted in a combined manner for each individual patient sample. To this end, the Bayesian pathway activity models were used as described in the above-mentioned published international patent applications using the long groups of PI3K and NFkB target genes.

Subsequently, two sub-groups of patients were selected from the dataset with (1) short disease-free survival (DFS) time, <12 months, and (2) the longest DFS, >24 months (total n=81). 59 sample data from patients with an in-between DFS were kept separate (sub-group 3).

Figure 1:
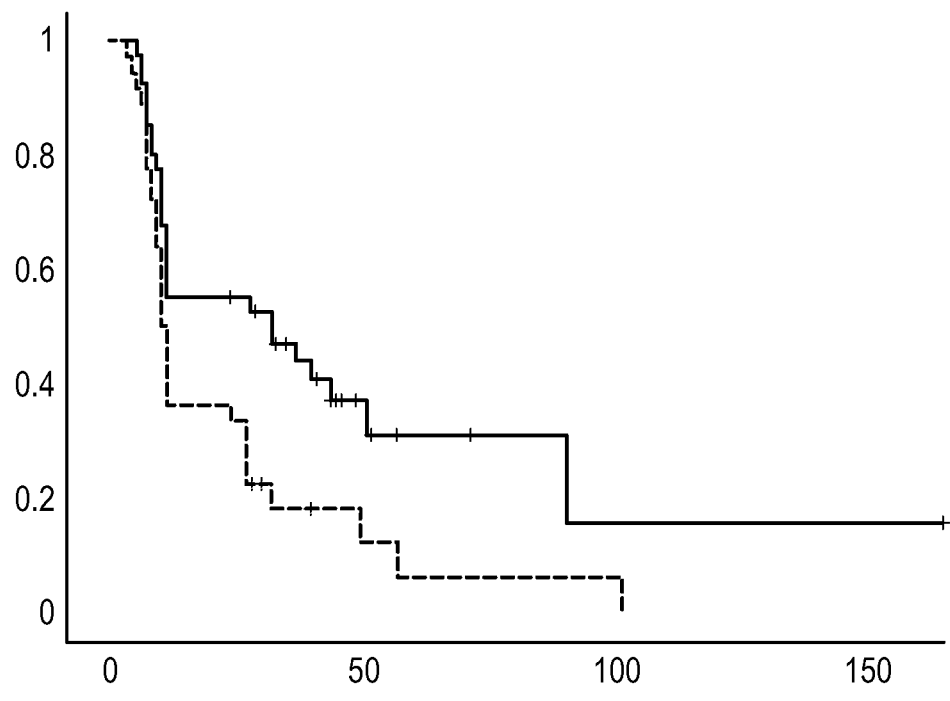
FIG. 1 shows Kaplan-Meier Curves of disease-free survival (DFS) for Cluster 1 and 2 high-grade serous ovarian cancer. Only patients were included with DFS<12 month or DFS>24 months. The upper solid line represents C1 patients (high FOXO/low PI3K activity, high NFkB activity), the lower dotted line represents C2 patients (low FOXO/high PI3K activity, low NFkB activity). Each '+' sign indicates a right censored patient, meaning that the follow-up was stopped (because the end of the study period was reached). Provided below the diagram are the numbers at risk (upper row represents C1 patients, lower row represents C2 patients).
Figure 1:

A k-means clustering was performed and resulted in two stable clusters: C1 with low PI3K pathway activity (high FOXO transcription factor activity scores) and high NFkB pathway scores (n=43 patient sample data), and C2, with a high PI3K pathway activity (low FOXO transcription factor activity scores) and low NFkB pathway activity (n=38). C1 was associated with a relatively favorable prognosis, reflected in a longer disease-free survival in the Kaplan-Meier curve analysis, and C2 was associated with a less favorable prognosis (p=0.011; FIG. 1).

Figure 2:
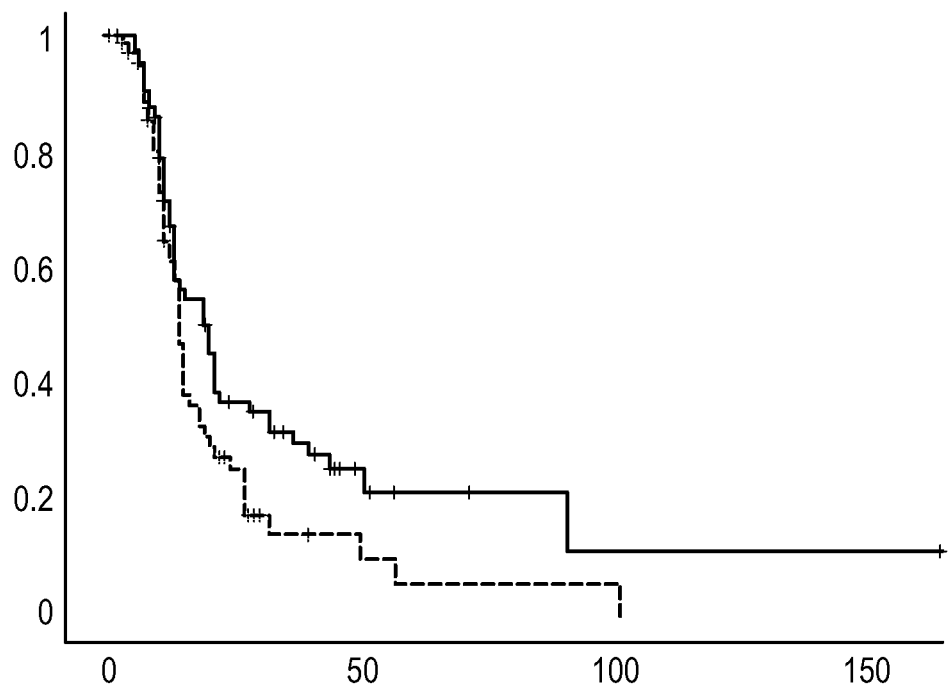
FIG. 2 shows Kaplan-Meier Curves of disease-free survival (DFS) for Cluster 1 and 2 high-grade serous ovarian cancer. All patients were included of whom a DFS was known. The upper line represents C1 patients (high FOXO/low PI3K activity, high NFkB activity), the lower line represents C2 patients (low FOXO/high PI3K activity, low NFkB activity). Each '+' sign indicates a right censored patient, meaning that the follow-up was stopped (because the end of the study period was reached). Provided below the diagram are the numbers at risk (upper row represents C1 patients, lower row represents C2 patients).
Figure 3:
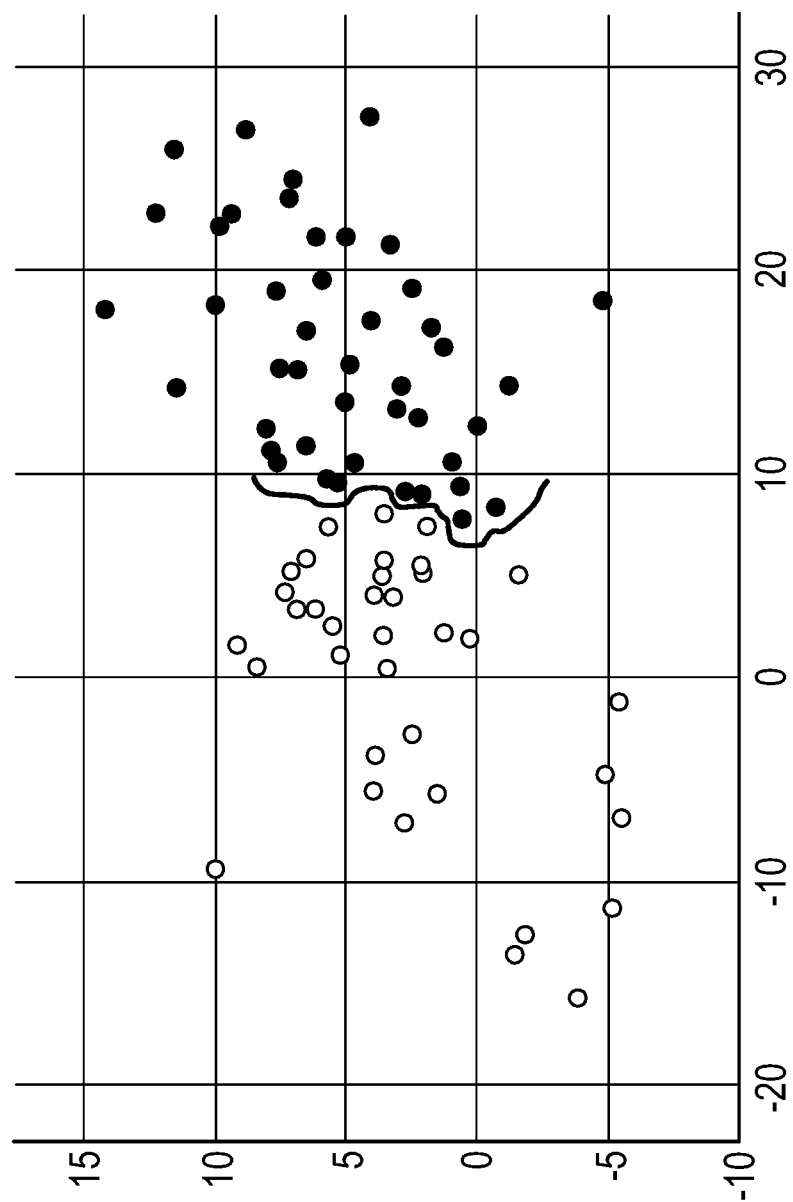
FIGS. 3 and 4 show the correlation between FOXO activity scores (ordinate) and NFkB activity scores (abscissa) (both as log 2odds) in short-term and long-term high-grade serous ovarian cancer disease-free survival (DFS). Lines were draw to distinguish the respective groups.
Figure 4:
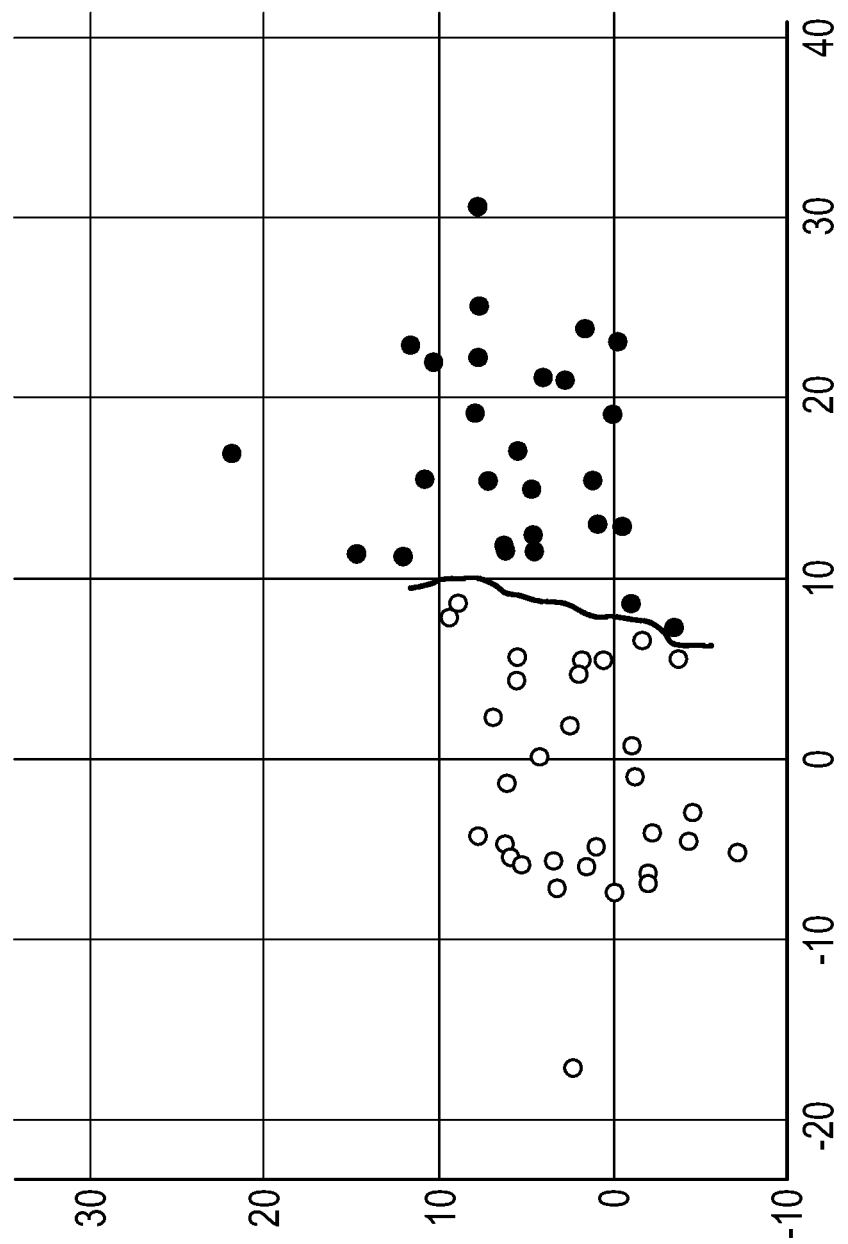

Subsequently, the best-fitting cluster (C1 or C2) was determined for the samples in group 3, and these were added to the Kaplan-Meier curve analysis. In this manner, 73 samples for C1 and 67 samples for C2 were available for the Kaplan-Meier analysis. Again, C1 showed up as the sub-group with the longest DFS and therefore best relative prognosis, and C2 was the group with the shortest DFS (p=0.036; FIG. 2). As can be seen from FIGS. 3 and 4, a correlation curve between FOXO activity scores (ordinate) and NFkB activity scores (abscissa) (both as log 2odds) with disease-free survival time (short-long) indicated shows the same result. FIG. 3: Cluster groups 1 and 2. FIG. 4: Results for groups 1 to 3 together, according to cluster designation. (In both diagrams, the black circles represent C1 patients and the white circles represent C2 patients.)

These results show that the combined activity of the FOXO transcription factor and the NFkB pathway are associated with a favorable prognosis, which may be due to a lower growth rate, for example, associated with apoptosis, as has been suggested to be conferred by NFkB-FOXO. FOXO3A is involved in the regulation of apoptosis which is important for the tumor-suppressive effect of these transcription factors. Thus, apoptosis is causally related to less aggressive tumor growth and a more favorable prognosis. In contrast, the PI3K pathway was known to be a growth factor pathway which plays a role in all kinds of cancer as a "survival pathway" to enable cell division, and amplify effects of other oncogenic signaling pathways that are active in the cell.

Based on these results a decision model may be derived for the determination of a prognosis for a subject diagnosed with high-grade serous ovarian cancer. For example, as shown in Table 1A, when the activity of the PI3K pathway is low (high FOXO transcription factor activity) and the activity of the NFkB pathway is high, it may be decided that the prognosis is favorable. In contrast, when the activity of the PI3K pathway is high (low FOXO transcription factor activity) and the activity of the NFkB pathway is low, it may be decided that the prognosis is unfavorable. When the activity of the PI3K pathway is low (high FOXO transcription factor activity) and the activity of the NFkB pathway is low or when the activity of the PI3K pathway is high (low FOXO transcription factor activity) and the activity of the NFkB pathway is high, it may be decided that the prognosis is intermediate.

The pathway and/or transcription factor activities provided by the pathway analysis may be represented in a quantitative manner as a numerical value (e.g., as a level or score) and whether the activity is high or low may be decided by comparing the numerical value with a suitably defined threshold. For example, in Table 1A, the activities of the NFkB pathway and of the FOXO transcription factor are represented by log 2odds scores. The activity of the NFkB pathway is then considered to be high if the score exceeds a threshold of 8 log 2odds and it is considered to be low if the score is below this threshold. The activity of the FOXO transcription factor, in this example, is considered to be high if the score exceeds a threshold of 3.5 log 2odds and it is considered to be low if the score is below this threshold.

As an alternative, the NFkB pathway activity score and the FOXO transcription factor activity score may be added together. A favorable prognosis may then be decided if the combined NFkB+FOXO activity is high. For example, considering the log 2odds scores of Table 1A, it may be decided that the prognosis is favorable if the sum of the scores exceeds a suitably defined upper threshold, e.g., 22, that the prognosis is unfavorable if the sums of the scores is below another suitably defined lower threshold, e.g., 2.5, and that the prognosis is intermediate if the sum of the scores is between the upper and lower threshold. It is also possible to make the intermediate prognosis more quantitative by calculating from the sum of the scores a probability value based on a linear interpolation between the upper and lower thresholds. The probability value can then indicate whether the intermediate prognosis is more likely favorable or unfavorable as well as to which extend, e.g., 10%, 40%, 80% or the like, it is likely favorable or unfavorable.

TABLE 1A

A decision model for the determination of a prognosis.

| | Favorable prognosis | Unfavorable prognosis | Intermediate prognosis | Intermediate Prognosis |
|---|---|---|---|---|
| NFkB pathway activity score | High (>8 log2odds score) | Low (<8 log2odds score) | High | Low |
| FOXO transcription factor activity score | High (>3.5 log2odds score) | Low (<3.5 log2odds score) | Low | high |

Other ways to determine the prognosis based on a combination of pathway activities as described herein are also envisioned, for example:

1. A cluster analysis, defining two clusters, with either NFkB pathway activity score/FOXO transcription factor activity score high or NFkB pathway activity score/FOXO transcription factor activity score low, may be performed as described above and the centroids for the activities may be determined (Table 1B). In order to determine the prediction for a subject, the distance (in two-dimensional space) to each of the centroids may be determined and the prognosis may be decided based on which of the centroids is closest. For example, if C1 is the cluster with the better relative prognosis, C2 is the cluster with the worse relative prognosis, c1 and c2 are the centroids of the clusters, respectively, and d1 and d2 are the distances to the centroids c1 and c2, it may be decided that the prognosis is favorable if d1<d2 and unfavorable if d2<d1.

2. An alternative to this approach would be to assign a probability of a favorable prognosis as d2/(d1+d2) and a corresponding probability of an unfavorable prognosis as d1/(d1+d2).

TABLE 1B

Clustering analysis results, defining two clusters, with either NFkB pathway activity score/FOXO transcription factor activity score high or NFkB pathway activity score/FOXO transcription factor activity score low, with log2odds values for activities in the centroids indicated. The number of cases in cluster 1 was 43, the number of cases in cluster 2 was 38. All 81 cases were valid with no cases missing. Based on these data a computational model can be made which determines the likelihood of a favorable prognosis.

|  | Cluster | |
| --- | --- | --- |
|  | 1 | 2 |
| FOXO (log2odds score) | 5.47757097 (~5.5) | 2.54638685 (~2.5) |
| NFkB (log2odds score) | 16.4684658 (~16.5) | 0.148962314 (~0) |

We described two cellular signaling pathway activity clusters in high-grade serous ovarian cancer with a difference in DFS. The low PI3K pathway activity (high FOXO transcription factor activity) and high NFkB pathway activity of the favorable prognosis cluster may indicate apoptosis, while the high PI3K pathway activity (low FOXO transcription factor activity) and low NFkB pathway activity of the unfavorable prognosis cluster may indicate high cell division. The patients with a high PI3K pathway activity are likely to benefit from PI3K pathway inhibiting treatment or (together with) potentially chemotherapy.

CDS Application

Figure 5:
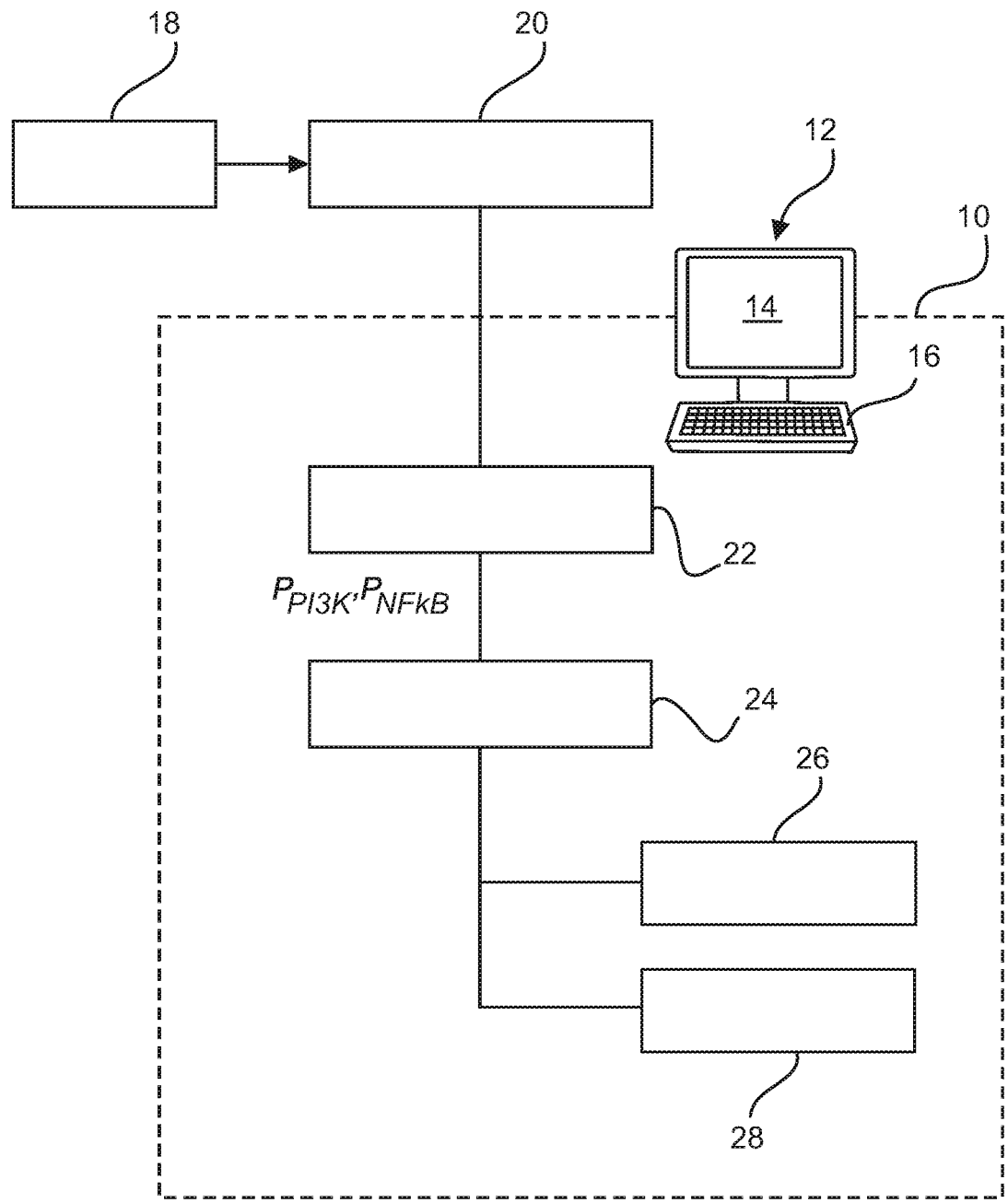
FIG. 5 diagrammatically shows a clinical decision support (CDS) system configured to determine a prognosis for a subject diagnosed with high-grade serous ovarian cancer, or to identify a subject diagnosed with high-grade serous ovarian cancer that will be suitable for a PI3K pathway targeting therapy or an NFkB pathway targeting therapy.

With reference to FIG. 5 (diagrammatically showing a clinical decision support (CDS) system configured to determine a prognosis for a subject diagnosed with high-grade serous ovarian cancer, or to identify a subject diagnosed with high-grade serous ovarian cancer that will be suitable for a PI3K pathway targeting therapy or an NFkB pathway targeting therapy, as described herein), a clinical decision support (CDS) system 10 is implemented as a suitably configured computer 12. The computer 12 may be configured to operate as the CDS system 10 by executing suitable software, firmware, or other instructions stored on a non-transitory storage medium (not shown), such as a hard drive or other magnetic storage medium, an optical disk or another optical storage medium, a random access memory (RAM), a read-only memory (ROM), a flash memory, or another electronic storage medium, a network server, or so forth.

While the illustrative CDS system 10 is embodied by the illustrative computer 12, more generally the CDS system may be embodied by a digital processing device or an apparatus comprising a digital processor configured to perform clinical decision support methods as set forth herein. For example, the digital processing device may be a handheld device (e.g., a personal data assistant or smartphone running a CDS application), a notebook computer, a desktop computer, a tablet computer or device, a remote network server, or so forth. The computer 12 or other digital processing device typically includes or is operatively connected with a display device 14 via which information including clinical decision support recommendations are displayed to medical personnel. The computer 12 or other digital processing device typically also includes or is operatively connected with one or more user input devices, such as an illustrative keyboard 16, or a mouse, a trackball, a trackpad, a touch-sensitive screen (possibly integrated with the display device 14), or another pointer-based user input device, via which medical personnel can input information such as operational commands for controlling the CDS system 10, data for use by the CDS system 10, or so forth.

The CDS system 10 receives as input information pertaining to a subject (e.g., a hospital patient, or an outpatient being treated by an oncologist, physician, or other medical personnel, or a person undergoing cancer screening or some other medical diagnosis who has been diagnosed with high-grade serous ovarian cancer). The CDS system 10 applies various data analysis algorithms to this input information in order to generate clinical decision support recommendations that are presented to medical personnel via the display device 14 (or via a voice synthesizer or other device providing human-perceptible output). In some embodiments, these algorithms may include applying a clinical guideline to the patient. A clinical guideline is a stored set of standard or "canonical" treatment recommendations, typically constructed based on recommendations of a panel of medical experts and optionally formatted in the form of a clinical "flowchart" to facilitate navigating through the clinical guideline. In various embodiments the data processing algorithms of the CDS 10 may additionally or alternatively include various diagnostic or clinical test algorithms that are performed on input information to extract clinical decision recommendations, such as machine learning methods disclosed herein.

In the illustrative CDS systems disclosed herein (e.g., CDS system 10), the CDS data analysis algorithms include one or more diagnostic or clinical test algorithms that are performed on input genomic and/or proteomic information acquired by one or more medical laboratories 18. These laboratories may be variously located "on-site", that is, at the hospital or other location where the subject is undergoing medical examination and/or treatment, or "off-site", e.g., a specialized and centralized laboratory that receives (via mail or another delivery service) a sample of the subject that has been extracted from the subject.

The sample is processed by the laboratory to generate genomic or proteomic information. For example, the sample may be processed using a microarray (also variously referred to in the art as a gene chip, DNA chip, biochip, or so forth) or by quantitative polymerase chain reaction (qPCR) processing to measure probative genomic or proteomic information such as expression levels of genes of interest, for example in the form of a level of messenger ribonucleic acid (mRNA) that is transcribed from the gene, or a level of a protein that is translated from the mRNA transcribed from the gene. As another example, the sample may be processed by a gene sequencing laboratory to generate sequences for deoxyribonucleic acid (DNA), or to generate an RNA sequence, copy number variation, methylation, or so forth. Other contemplated measurement approaches include immunohistochemistry (IHC), cytology, fluorescence in situ hybridization (FISH), proximity ligation assay or so forth, performed on a pathology slide. Other information that can be generated by microarray processing, mass spectrometry, gene sequencing, or other laboratory techniques includes methylation information. Various combinations of such genomic and/or proteomic measurements may also be performed.

In some embodiments, the medical laboratories 18 perform a number of standardized data acquisitions on the sample of the subject, so as to generate a large quantity of genomic and/or proteomic data. For example, the standardized data acquisition techniques may generate an (optionally aligned) DNA sequence for one or more chromosomes or chromosome portions, or for the entire genome. Applying a standard microarray can generate thousands or tens of thousands of data items such as expression levels for a large number of genes, various methylation data, and so forth. Similarly, PCR-based measurements can be used to measure the expression level of a selection of genes. This plethora of genomic and/or proteomic data, or selected portions thereof, are input to the CDS system 10 to be processed so as to develop clinically useful information for formulating clinical decision support recommendations.

The disclosed CDS systems and related methods relate to processing of genomic and/or proteomic data to assess activity of cellular signaling pathways including a PI3K pathway and an NFkB pathway and to determine a prognosis for a subject diagnosed with high-grade serous ovarian cancer, or to identify a subject diagnosed with high-grade serous ovarian cancer that will be suitable for a PI3K pathway targeting therapy or an NFkB pathway targeting therapy, as diclosed herein. However, it is to be understood that the disclosed CDS systems (e.g., CDS system 10) may optionally further include diverse additional capabilities, such as generating clinical decision support recommendations in accordance with stored clinical guidelines based on various patient data such as vital sign monitoring data, patient history data, patient demographic data (e.g., gender, age, or so forth), patient medical imaging data, or so forth. Alternatively, in some embodiments the capabilities of the CDS system 10 may be limited to only performing genomic and/or proteomic data to assess activity of cellular signaling pathways including a PI3K pathway and an NFkB pathway and to determine a prognosis for a subject diagnosed with high-grade serous ovarian cancer, or to identify a subject diagnosed with high-grade serous ovarian cancer that will be suitable for a PI3K pathway targeting therapy or an NFkB pathway targeting therapy, as disclosed herein.

With continuing reference to exemplary FIG. 5, the CDS system 10 infers 22 the activities ($P_{PI3K}$, $P_{NFkB}$) of at least two cellular signaling pathways including a PI3K pathway and an NFkB pathway in a sample of the subject based on, but not restricted to, the expression levels 20 of three or more target genes of the cellular signaling pathways measured in the sample of the subject.

Measurement of mRNA expression levels of genes that encode for regulatory proteins of the cellular signaling pathway, such as an intermediate protein that is part of a protein cascade forming the cellular signaling pathway, is an indirect measure of the regulatory protein expression level and may or may not correlate strongly with the actual regulatory protein expression level (much less with the overall activity of the cellular signaling pathway). The cellular signaling pathway directly regulates the transcription of the target genes—hence, the expression levels of mRNA transcribed from the target genes is a direct result of this regulatory activity. Hence, the CDS system 10 infers activity of the at least two cellular signaling pathways based on expression levels of three or more target genes (mRNA or protein level as a surrogate measurement) of the cellular signaling pathways. This ensures that the CDS system 10 infers the activity of the pathway based on direct information provided by the measured expression levels of the target gene(s).

The inferred pathway activities are then used to determine 24 a prognosis for the subject diagnosed with high-grade serous ovarian cancer. The determination of the prognosis may be based on a decision model, as exemplarily described above.

Based on the determined prognosis, the CDS system 10, in this example, assigns 26 the subject to at least one of a plurality of prognosis groups, as for example: "favorable", "intermediate" or "unfavorable" prognosis.

The CDS system 10 may also be adapted to identify 24 a subject diagnosed with high-grade serous ovarian cancer that will be suitable for a PI3K pathway targeting therapy or an NFkB pathway targeting therapy. The inferred pathway activities for the subject are used in the identification. If the subject is identified as being suitable for a PI3K pathway targeting therapy or an NFkB pathway targeting therapy, an oncologist, physician, or other medical personnel may provide 28 to the identified subject the PI3K pathway targeting therapy or the NFkB pathway targeting therapy.

This document describes several preferred embodiments. Modifications and alterations may occur to others upon reading and understanding the preceding detailed description. It is intended that the document is construed as including all such modifications and alterations insofar as they come within the scope of the appended claims or the equivalents thereof.

In the claims, the word "comprising" does not exclude other elements or steps, and the indefinite article "a" or "an" does not exclude a plurality. A single unit or device may fulfill the functions of several items recited in the claims. The mere fact that certain measures are recited in mutually different dependent claims does not indicate that a combination of these measures cannot be used to advantage.

Calculations like the determination of the prognosis performed by one or several units or devices can be performed by any other number of units or devices. It shall be understood that a preferred embodiment of the present invention can also be any combination of the dependent claims or above embodiments with the respective independent claim.

These and other aspects of the invention will be apparent from and elucidated with reference to the embodiments described hereinafter.

The invention claimed is:

1. A method for treating a human subject diagnosed with high-grade serous ovarian cancer, wherein the method comprises:
  receiving a sample obtained from an ovarian tumor of the subject;
  determining a favorable prognosis for the subject based on activities of at least two cellular signaling pathways including a phosphatidylinositide 3-kinase (PI3K) pathway and a nuclear factor-kappa B (NFkB or NFκB) pathway in the sample of the subject, wherein the activities of the at least two cellular signaling pathways in the sample are inferred by a method comprising:

receiving expression levels of three or more target genes for each of said respective cellular signaling pathways measured in the sample, and wherein:

determining an activity level of a cellular signaling pathway associated transcription factor (TF) element, the cellular signaling pathway associated TF element controlling transcription of the three or more target genes, the determining being based on a calibrated mathematical pathway model relating the expression levels of the three or more target genes to the activity level of the TF element, and, inferring the activity of the respective cellular signaling pathway based on the determined activity level of the cellular signaling pathway associated TF element:

wherein the three or more PI3K pathway target genes are selected from the group consisting of: AGRP, BCL2L11, BCL6, BNIP3, BTG1, CAT, CAV1, CCND1, CCND2, CCNG2, CDK 1A, CDK 1B, ESR1, FASLG, FBX032, GADD45A, INSR, MXIL NOS3, PCK1, POMC, PPARGCIA, PRDX3, RBL2, SOD2 and TNFSF10, and wherein the three or more NFkB pathway target genes are selected from the group consisting of: BCL2L1, BIRC3, CCL2, CCL3, CCL4, CCLS, CCL20, CCL22, CX3CL1, CXCL1, CXCL2, CXCL3, ICAM1, 1L1B, 1L6, 1L8, IRF1, MMP9, NFKB2, NFKBIA, NFKBIE, PTGS2, SELE, STATSA, TNF, TNFAIP2, TNIP1, TRAF1, and VCAM1, and wherein, when the activity of the PI3K pathway is low and the activity of the NFkB pathway is high, the prognosis for the subject is determined to be favorable, and administering, in response to determining a favorable prognosis for the subject, a PI3K pathway targeting therapy configured to mediate activity of the PI3K pathway and/or a NFkB pathway targeting therapy configured to inhibit the activity of the NFkB pathway.

2. The method of claim 1, wherein the calibrated mathematical pathway model is a probabilistic model based on conditional probabilities relating the activity level of the TF element and the expression levels of the three or more target genes, or wherein the mathematical pathway model is based on one or more linear combination(s) of the expression levels of the three or more target genes.

3. A method for treating a human subject diagnosed with high-grade serous ovarian cancer identified as being suitable for a PI3K pathway targeting therapy or a nuclear factor-kappa B (NFkB or NFκB) pathway targeting therapy, wherein the method comprises:

receiving a favorable diagnosis for the subject based on inferred activities of at least two cellular signaling pathways including a phosphatidylinositide 3-kinase (PI3K) pathway and an NFkB pathway in a sample obtained from an ovarian tumor of the subject, wherein the activities of the at least two cellular signaling pathways in the sample are inferred by a method comprising:

receiving expression levels of three or more target genes for each of said respective cellular signaling pathways measured in the sample, determining an activity level of a cellular signaling pathway associated transcription factor (TF) element, the cellular signaling pathway associated TF element controlling transcription of the three or more target genes, the determining being based on a calibrated mathematical pathway model relating the expression levels of the three or more target genes to the activity level of the TF element, and, inferring the activity of the respective cellular signaling pathway based on the determined activity level of the cellular signaling pathway associated TF element:

wherein the three or more PI3K pathway target genes are selected from the group consisting of: AGRP, BCL2L11, BCL6, BNIP3, BTG1, CAT, CAV1, CCND1, CCND2, CCNG2, CDK 1A, CDK 1B, ESR1, FASLG, FBX032, GADD45A, INSR, MXIL NOS3, PCK1, POMC, PPARGCIA, PRDX3, RBL2, SOD2 and TNFSF10, and wherein the three or more NFkB pathway target genes are selected from the group consisting of: BCL2L1, BIRC3, CCL2, CCL3, CCL4, CCLS, CCL20, CCL22, CX3CL1, CXCL1, CXCL2, CXCL3, ICAM1, IL1B, IL6, IL8, IRF1, MMP9, NFKB2, NFKBIA, NFKBIE, PTGS2, SELE, STATSA, TNF, TNFAIP2, TNIP1, TRAF1, and VCAM1, wherein, when the activity of the PI3K pathway is low and the activity of the NFkB pathway is high, the prognosis for the subject is determined to be favorable, and administering, in response to determining a favorable prognosis for the subject, a PI3K pathway targeting therapy configured to mediate activity of the PI3K pathway and/or a NFkB pathway targeting therapy configured to inhibit the activity of the NFkB pathway.

4. The method of claim 1, further comprising the step of:
recommending, based on the determined favorable prognosis, a PI3K pathway targeting therapy, an NFkB pathway targeting therapy, or both therapies for the subject diagnosed with high-grade serous ovarian cancer.

5. The method of claim 3, further comprising the step of:
recommending a PI3K pathway targeting therapy, an NFkB pathway targeting therapy, or both therapies for a subject identified as being suitable for a PI3K pathway targeting therapy or an NFkB pathway targeting therapy.

6. The method of claim 3, wherein the calibrated mathematical pathway model is a probabilistic model based on conditional probabilities relating the activity level of the TF element and the expression levels of the three or more target genes, or wherein the mathematical pathway model is based on one or more linear combination(s) of the expression levels of the three or more target genes.

7. A method for treating a human subject diagnosed with high-grade serous ovarian cancer, wherein the method comprises:

receiving a sample obtained from an ovarian tumor of the subject;

determining a favorable prognosis for the subject based on activities of a phosphatidylinositide 3-kinase (PI3K) cellular signaling pathway and a nuclear factor-kappa B (NFkB or NEκB) cellular signaling pathway in the sample of the subject, wherein the activities of the PI3K and NFkb cellular signaling pathways in the sample determined by a method comprising:

receiving expression levels of three or more target genes for each of said respective cellular signaling pathways measured in the sample;

determining an activity level of a cellular signaling pathway associated transcription factor (TF) element, the cellular signaling pathway associated TF element controlling transcription of the three or more target genes, the determining being based on a calibrated mathematical pathway model relating the expression levels of the three or more target genes to the activity level of the TF element, and, inferring the activity of the respective cellular signaling pathway based on the determined activity level of the cellular signaling pathway associated TF element;

wherein the three or more PI3K pathway target genes are selected from the group consisting of: AGRP, BCL2L11, BCL6, BNIP3, BTG1, CAT, CAV1, CCND1, CCND2, CCNG2, CDK 1A, CDK 1B, ESR1, FASLG, FBX032, GADD45A, INSR, MXI1, NOS3, PCK1, POMC, PPARGCIA, PRDX3, RBL2, SOD2 and TNFSF10, and wherein the three or more NFlcB pathway target genes are selected from the group consisting of: BCL2L1, BIRC3, CCL2, CCL3, CCL4, CCLS, CCL20, CCL22, CX3CL1, CXCL1, CXCL2, CXCL3, ICAM1, 1L1B, 1L6, 1L8, IRF1, MMP9, NFKB2, NFKBIA, NFKBIE, PTGS2, SELE, STATSA, TNF, TNFAIP2, TNIP1, TRAF1, and VCAM1, and wherein, when the activity of the PI3K pathway is low and the activity of the NFlcB pathway is high, the prognosis is determined to be favorable, and administering, in response to determining a favorable prognosis for the subject, a PI3K pathway targeting therapy configured to mediate activity of the PI3K pathway and/or a NFlcB pathway targeting therapy configured to inhibit the activity of the NFkB pathway.

8. The method of claim 7, wherein the calibrated mathematical pathway model is a probabilistic model based on conditional probabilities relating the activity level of the TF element and the expression levels of the three or more target genes, or wherein the mathematical pathway model is based on one or more linear combination(s) of the expression levels of the three or more target genes.

* * * * *